US008524497B2

(12) United States Patent  (10) Patent No.: US 8,524,497 B2
Reiter et al.  (45) Date of Patent: Sep. 3, 2013

(54) ANIMAL PROTEIN FREE MEDIA FOR CULTIVATION OF CELLS

(75) Inventors: Manfred Reiter, Vienna (AT); Wolfgang Mundt, Vienna (AT); Leopold Grillberger, Vienna (AT); Barbara Kraus, Obersdorf (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/102,765

(22) Filed: May 6, 2011

(65) Prior Publication Data

US 2011/0217772 A1 Sep. 8, 2011

Related U.S. Application Data

(62) Division of application No. 10/614,037, filed on Jul. 8, 2003, now Pat. No. 7,955,833.

(60) Provisional application No. 60/394,243, filed on Jul. 9, 2002.

(51) Int. Cl.
 *C12N 5/07* (2010.01)
(52) U.S. Cl.
 USPC .......................................... 435/395; 435/404
(58) Field of Classification Search
 None
 See application file for complete search history.

(56) References Cited

U.S. PATENT DOCUMENTS

| | | |
|---|---|---|
| 4,431,629 A | 2/1984 | Olsen |
| 4,443,540 A | 4/1984 | Chervan et al. |
| 4,767,704 A | 8/1988 | Cleveland et al. |
| 4,978,616 A | 12/1990 | Dean, Jr. et al. |
| 5,122,469 A | 6/1992 | Mather et al. |
| 5,316,938 A | 5/1994 | Keen et al. |
| 5,378,612 A | 1/1995 | Nakashima et al. |
| 5,393,668 A | 2/1995 | Cinatl et al. |
| 5,441,868 A | 8/1995 | Lin |
| 5,573,937 A | 11/1996 | Shinmoto et al. |
| 5,633,162 A | 5/1997 | Keen et al. |
| 5,719,050 A | 2/1998 | Hashimoto et al. |
| 5,741,705 A | 4/1998 | Blom et al. |
| 5,753,489 A | 5/1998 | Kistner et al. |
| 5,789,247 A | 8/1998 | Ballay et al. |
| 5,811,299 A | 9/1998 | Renner et al. |
| 5,851,800 A | 12/1998 | Adamson et al. |
| 5,885,835 A | 3/1999 | Blom et al. |
| 6,048,728 A | 4/2000 | Inlow et al. |
| 6,100,061 A | 8/2000 | Reiter et al. |
| 6,406,909 B1 | 6/2002 | Shibuya et al. |
| 6,475,725 B1 | 11/2002 | Reiter et al. |
| 2002/0182679 A1 | 12/2002 | Reiter et al. |
| 2003/0203448 A1 | 10/2003 | Reiter et al. |

FOREIGN PATENT DOCUMENTS

| | | |
|---|---|---|
| AT | 1659/99 A | 9/1999 |
| AU | 78958/98 A | 10/1998 |
| CA | 2161517 A1 | 11/1994 |
| EP | 0 160 457 B1 | 11/1985 |
| EP | 0 481 791 A2 | 4/1992 |
| EP | 0 485 689 A1 | 5/1992 |
| EP | 0 631 731 A1 | 1/1995 |
| EP | 0 666 312 A1 | 8/1995 |
| EP | 0 711 835 A1 | 5/1996 |
| EP | 0 872 487 A2 | 10/1998 |
| EP | 00 120 89636.6 | 9/2000 |
| FR | 2 196 386 A | 3/1974 |
| JP | 3-244391 | 10/1991 |
| JP | 4-316484 | 11/1992 |
| JP | 5-123178 A | 5/1993 |
| JP | 7-039386 A | 2/1995 |
| JP | 2-859679 B2 | 2/1999 |
| JP | H01-211488 A | 8/1999 |
| JP | 201-211878 A | 8/2001 |
| WO | WO 85/02610 A1 | 6/1985 |
| WO | WO 86/04920 A1 | 8/1986 |
| WO | WO 88/00967 A1 | 2/1988 |
| WO | WO 89/00192 A1 | 1/1989 |
| WO | WO 91/09122 A1 | 6/1991 |
| WO | WO 91/10726 A1 | 7/1991 |
| WO | WO 94/25599 A1 | 11/1994 |
| WO | WO 96/07730 A2 | 3/1996 |
| WO | WO 96/07730 A3 | 3/1996 |
| WO | WO 96/15231 A1 | 5/1996 |
| WO | WO 96/18734 A1 | 6/1996 |
| WO | WO 96/26266 A1 | 8/1996 |
| WO | WO 96/40866 A1 | 12/1996 |
| WO | WO 97/05240 A1 | 2/1997 |
| WO | WO 98/08934 A1 | 3/1998 |
| WO | WO 98/15614 A1 | 4/1998 |

(Continued)

OTHER PUBLICATIONS

Nohara et al., J. Biochem. 125:343-347, 1999.*
Frazzati-Gallina et la., J. Biotech., 92:67-62, 2001.*
Berg, D.T. et al.; "High-Level Expression of Secreted Proteins from Cells Adapted to Serum-Free Suspension Culture"; *BioTechniques*; 1993; vol. 14(6); pp. 972-978.
Bielicki, J. et al.; "Recombinant Human Sulphamidase: Expression, Amplification, Purification and Characterization"; 1998; *Biochem. J.*; vol. 329; pp. 145-150.
Brown, M.E. et al.; "Process Development for the Production of Recombinant Antibodies Using the Glutamine Synthetase (GS) System"; 1992; *Cytotechnology*; vol. 9; pp. 231-236.
Burger, C. et al.; "An Integrated Strategy for the Process Development of a Recombinant Antibody-Cytokine Fusion Protein Expressed in BHK Cells"; 1999; *Appl. Microbiol. Biotechnol.*; vol. 52; pp. 345-353.

(Continued)

Primary Examiner — Nancy T Vogel
(74) Attorney, Agent, or Firm — Kilpatrick Townsend & Stockton LLP

(57) ABSTRACT

The present invention relates to animal protein free cell culture media comprising a combination of non-animal derived peptides derived from soy hydrolysate and yeast hydrolysate. The invention also provides an animal protein free culture process, wherein cells are cultivated, propagated and passaged without animal-derived components. This process is useful for cultivating cells, such as recombinant cells or cells infected with a virus, and for production biological products by cell culture processes under conditions devoid of animal protein components.

12 Claims, No Drawings

(56) References Cited

FOREIGN PATENT DOCUMENTS

| WO | WO 98/54296 A1 | 12/1998 |
|---|---|---|
| WO | WO 99/05268 A1 | 2/1999 |
| WO | WO 99/47648 A2 | 9/1999 |
| WO | WO 99/57246 A1 | 11/1999 |
| WO | WO 00/03000 A2 | 1/2000 |
| WO | WO 01/11021 A1 | 2/2001 |
| WO | WO 01/14529 A1 | 3/2001 |
| WO | WO 01/23527 A1 | 4/2001 |
| WO | WO 02/24876 A2 | 3/2002 |
| WO | WO 02/24876 A3 | 3/2002 |
| WO | WO 2004/005493 A1 | 1/2004 |

OTHER PUBLICATIONS

Cartier, M. and Stanners, C.P.; "Stable, High-Level Expression of a Carcinoembryonic Antigen-encoding cDNA After Transfection and Amplification with the Dominant and Selectable Asparagine Synthetase Marker"; 1990; *Gene*; vol. 95; pp. 223-230.

Cole, E.S. et al.; "Recombinant Human Thyroid Stimulating Hormone: Development of a Biotechnology Product for Detection of Metastatic Lesions of Thyroid Carcinoma"; Sep. 1993; *Biotechnology*; vol. 11; pp. 1014-1024.

Cruz, H.J. et al.; "Adaptation of BHK Cells Producing a Recombinant Protein to Serum-Free Media and Protein-Free Medium"; 1998; *Cytotechnology*; vol. 26; pp. 59-64.

Donaldson, M.S. and Sculer, M.L.; "Low-Cost Serum-Free Medium for the BTI-Tn5B1-4 Insect Cell Line"; 1998; *Biotechnol. Prog.*; vol. 14; pp. 573-579.

Doyle, A. et al. eds.; "Cloning"; Part 4D Module 4D1 in *Cell & Tissue Culture: Laboratory Procedures*; 1998; John Wiley & Sons; London; Cloning Techniques (Non-hybridoma Related); pp. 4D:1.1-4D:1.9.

Eagle, H.; "Amino Acid Metabolism in Mammalian Cell Cultures"; Aug. 21, 1939; *Science*; vol. 130; pp. 432-437.

Farrell, P.J. et al.; "High-Level Expression of Secreted Glycoproteins in Transformed Lepidopteran Insect Cells Using a Novel Expression Vector"; Dec. 20, 1998; *Biotechnology and Bioengineering*; vol. 60(6); pp. 656-663.

Faure, T. et al.; "Stable Expression of Coagulation Factors FVIII and Fix in Recombinant Chinese Hamster Ovary Cells"; 1989; Meeting Info. 9$^{th}$ General Meeting of the European Society for Animal Cell Technology; Knokke (Belgium); 1988; pp. 481-488.

Field, R.P. et al.; "Production of a Chimeric Antibody for Tumour Imaging and Therapy From Chinese Hamster Ovary (CHO) and Myeloma Cells"; May 1990; *Proceedings of the 10$^{th}$ ESACT Meeting*; pp. 742-744.

Fischer, B. et al.; "Comparison of N-Glycan Pattern of Recombinant Human Coagulation Factors II and IX Expressed in Chinese Hamster Ovary (CHO) and African Green Monkey (Vero) Cells"; 1996; *J. Thrombos. and Trombolys.*; vol. 3; pp. 57-62.

Fischer, B.E. et al.; "Biochemical and Functional Characterization of Recombinant von Willebrand Factor Produced on a Large Scale"; 1997; *CMLS*; vol. 53; pp. 943-950.

Fischer, B.E. et al.; "Structural Analysis of Recombinant von Willebrand Factor Produced at Industrial Scale Fermentation of Transformed CHO Cells Co-expressing Recombinant Furin"; 1995; *FEBS Letters*; vol. 375; pp. 259-262.

Fischer et al.; "Structural Analysis of Recombinant von Willebrand Factor: Identification of Hetero- and Homo-Dimers"; 1994; *FEBS Letters*; vol. 351; pp. 345-348.

Franek, F. et al.; "Plant Protein Hydrolysates: Preparation of Defined Peptide Fractions Promoting Growth and Production in Animal Cells Cultures"; 2000; *Biotechnol. Prog.*; vol. 16(5); pp. 688-692.

Freshney, R.I.; "The Culture Environment: Substrate, Gas Phase, Medium, and Temperature"; Chapter 7 in *Culture of Animal Cells a Manual of Basic Technique*, 2$^{nd}$ Edition; 1987; pp. 57-84.

Friedman, J.S. et al.; "High Expression in Mammalian Cells Without Amplification"; Apr. 1989; *Biotechnology*; vol. 7; pp. 359-362.

Gandor, C.; "Amplification and Expression of Recombinant Genes in Serum-Independent Chinese Hamster Ovary Cells"; 1995; *FEBS Letters*; vol. 377; pp. 290-294.

Gorfien, S.F. et al.; "Recombinant Protein Production by CHO Cells Cultured in a Chemically Defined Medium"; 1996; presented at JAACT, Yokohama: Japan; 16 pages.

Haldankar, R, et al.; "Stable Production of a Human Growth Hormone Antagonist From CHO Cells Adapted to Serum-Free Suspension Culture"; 1999; *Biotechnol. Prog.*; vol. 15(3); pp. 336-346.

Ham, R.G.; "Clonal Growth of Mammalian Cells in a Chemically Defined, Synthetic Medium"; 1965; *PNAS*. vol. 53; pp. 288-293.

Harant, H. et al.; "Two-Dimensional Electrophoresis as a Tool for Control of Quality and Consistency in Production Systems Using Animal Cells"; 1992; *Cytotechnology*; vol. 8; pp. 119-127.

Harrison, S. et al.; "The Manufacturing Process for Recombinant Factor IX"; Apr. 1998. *Seminars in Hematology*; vol. 35(2), Suppl. 2; pp. 4-10.

Hassell, T. et al.; "Stability of Production of Recombinant Antibodies from Glutamine Synthetase Amplified CHO and NS0 Cell Lines"; 1992; *Animal Cell Technology: Developments, Processes and Products*, 11$^{th}$ ESACT Meeting; pp. 42-47.

Heidemann, R. et al.; "The Use of Peptones as Medium Additives for High-Density Perfusion Cultures of Animal Cells"; Poster Presented at the 16th ESACT Meeting, Apr. 25-29, 1999, Lugano, Switzerland; 3 pages.

Heidemann, R. et al.; "The Use of Peptones as Medium Additives for the Production of a Recombinant Therapeutic Protein in High Density Perfusion Cultures of Mammalian Cells"; 2000; *Cytotechnology*; vol. 32; pp. 157-167.

Hsieh, C.M. et al.; "The Effect of Soy Protein Hydrolyzates on Fermentation by *Lactobacillus amylovorus*"; 1999; *Process Biochemistry*; vol. 34; pp. 173-179.

Inoue, Y. et al.; "Production of Recombinant Human Monoclonal Antibody Using *ras*-Amplified BHK-21 Cells in a Protein-free Medium"; 1996; *Biosci. Biotech. Biochem.*; vol. 60(5); pp. 811-817.

Ito, Y. et al.; "Protein-Free Cell Culture on an Artificial Substrate with Covalently Immobilized Insulin"; 1996; *Proc. Natl. Acad. Sci. USA*; vol. 93; pp. 3598-3601.

Jan, D.C-H. et al.; "Peptone, a Low-Cost Growth-Promoting Nutrient for Intensive Animal Cell Culture"; *Cytotechnology*; vol. 16; pp. 17-26, 1994.

Jin, B.R. et al.; "Production Kinetics and Stability of a Transfectoma Cell Line Secreting Murine/Human Chimeric Antibody"; 1993; *Mol. Cells*; vol. 3; pp. 233-237.

Kadouri, A. et al.; "Dynamic Changes in Cytokine Secretion by Stromal Cells During Prolonged Maintenance Under Protein-Free Conditions,"; 1992; *International Journal of Cell Cloning*; vol. 10; pp. 299-308.

Katinger, H. et al.; "Long-Term Stability of Continuously Perfused Animal Cells Immobilized on Novel Macroporous Microcarriers"; 1996; *Adv. Molecul. Cell Biol.*; vol. 15A; pp. 193-207.

Katsuta, H. et al.; "Effects of Polyamines on the Proliferation of Mammalian Cells in Tissue Culture"; 1975; *The Japanese Journal of Experimental Medicine*; vol. 45(5); pp. 345-354.

Katsuta, H. and Takaoka, T.; "Amino Acid Requirements of a Substrain of Strain L Cells (Mouse Fibroblasts) in Protein-Free Chemically Defined Synthetic Media"; 1960; *Japan. J. Exp. Med.*; vol. 30; pp. 235-259.

Kaufman, K. et al.; "Effect of von Willebrand Factor Coexpression on the Synthesis and Secretion of Factor VIII in Chinese Hamster Ovary Cells"; 1989; *Molecul. Cellul. Biol.*; vol. 9(3); pp. 1233-1242.

Keay, L.; "Autoclavable Low Cost Serum-Free Cell Culture Media: the Growth of Established Cell Lines and Production of Viruses"; 1976; *Biotechnology and Bioengineering*; vol. XVIII; pp. 363-382.

Keay, L.; "Autoclavable Low Cost Serum-Free Cell Culture Media. The Growth of L Cells and BHK Cells on Peptones"; 1975; *Biotechnology and Bioengineering*; vol. XVII; pp. 745-764.

Keen, M.J. and Rapson, N.T.; "Development of a Serum-Free Culture Medium for the Large Scale Production of Recombinant Protein From a Chinese Hamster Ovary Cell Line"; 1995; *Cytotechnology*; vol. 17; pp. 153-163.

Kim, S.J. et al.; "Characterization of Chimeric Antibody Producing CHO Cells in the Course of Dihydrofolate Reductase-Mediated Gene Amplification and Their Stability in the Absence of Selective Pressure"; Apr. 5, 1998; *Biotechnology and Bioengineering*; vol. 58(1); pp. 73-84.

Kim, N.S. et al.; "Clonal Variability Within Dihydrofolate Reductase-Mediated Gene Amplified Chinese Hamster Ovary Cells: Stability in the Absence of Selective Pressure"; Dec. 20, 1998; *Biotechnology and Bioengineering*; vol. 60(6); pp. 679-688.

Kwon, M.S. et al.; "Use of Plant-Derived Protein Hydrolysates for Enhancing Growth of *Bombyx mori* (Silkworm) Insect Cells in Suspension Culture"; 2005; *Biotechnology and Applied Biochemistry*; vol. 42; pp. 1-7.

Lee, K.H. et al.; "Deregulated Expression of Cloned Transcription Factor E2F-1 in Chinese Hamster Ovary Cells Shifts Protein Patterns and Activates Growth in Protein-Free Medium"; 1996; *Biotechnol. Bioeng.*; vol. 50; pp. 273-279.

Luchette, C. et al.; "Isolation and Characterization of a CHO Cell Line Expressing rhFSH in Low Protein and Protein-Free Media"; 1997; *Animal Cell Technology*; pp. 669-674.

Merten, O.-W. et al.; "Production of Influenza Virus in Serum-Free Mammalian Cell Cultures"; 1999; *Dev. Biol. Stand.*; vol. 98; pp. 23-37.

Merten, O.-W. et al.; "The New Medium MDSS2N, Free of Any Animal Protein Supports Cell Growth and Production of Various Viruses"; 1999; *Cytotechnology*; vol. 30; pp. 191-201.

Merten, O.-W.; "Safety Issues of Animal Products Used in Serum-Free Media"; 1999; *Dev. Biol. Stand.*; vol. 99; pp. 167-180.

Miyaji, H. et al.; "Efficient Expression of Human Beta-interferon in Namalwa KJM-1 Cells Adapted to Serum-free Medium by a dhfr Gene Coamplification Method"; 1990; *Cytotechnology*; vol. 4; pp. 173-180.

Miyaji, H. et al.; "Expression of Human Beta-interferon in Namalwa KJM-1 Which Was Adapted to Serum-free Medium";1990; *Cytotechnology*; vol. 37; pp. 133-140.

Motz, M. et al.; "Expression of the Epstein-Barr Virus Major Membrane Proteins in Chinese Hamster Ovary Cells"; 1986; *Gene*; vol. 44(2-3); pp. 353-359; Abstract, 1 page.

Murhammer, D.W. and Gooche, C.F.; "Structural Features of Nonionic Polyglycol Polymer Molecules Responsible for the Protective Effect in Sparged Animal Cell Bioreactors"; 1990; *Biotechnol. Prog.*; vol. 6; pp. 142-146.

Nilsson, K. et al.; "Microcarrier Culture of Recombinant Chinese Hamster Ovary Cells for Production of Human Immune Interferon and Human Tissue-Type Plasminogen Activator"; 1988; *Appl. Microbiol. Biotechnol.*; vol. 27; pp. 366-371.

Nyberg, G.B. et al.; "Metabolism of Peptide Amino Acids by Chinese Hamster Ovary Cells Grown in a Complex Medium"; Feb. 5, 1999; *Biotechnology and Bioengineering*; vol. 62(3); pp. 324-335.

Ochiai, M. et al.; "Endotoxin Content in *Haemophilus influenzae* Type b Vaccine"; 2004; *Jpn. J. Infect. Dis.*; vol. 57; pp. 58-59.

Ogata, M. et al.; "High-Level Expression of Recombinant Human Soluble Thrombomodulin in serum-Free Medium by CHO-K1 Cells"; 1993; *Appl. Microbiol. Biotechnol.*; vol. 38; pp. 520-525.

Pak, S.C.O. et al.; "Super-CHO—A Cell Line Capable of Autocrine Growth Under Fully Defined Protein-Free Conditions"; 1996; *Cytotechnology*; vol. 22; pp. 139-146.

Paterson, T. et al.; "Approaches to Maximizing Stable Expression of α1-Antitrypsin in Transformed CHO Cells"; 1994; *Appl. Microbiol. Biotechnol.*; vol. 40; pp. 691-698.

Pu, H. et al.; "Rapid Establishment of High-Producing Cell Lines Using Dicistronic Vectors with Glutamine Synthetase as the Selection Marker"; 1998; *Molecular Biotechnology*, vol. 10; pp. 17-25.

Qi, Y.M. et al.; "Evaluation of a Simple Protein Free Medium That Supports High Levels of Monoclonal Antibody Production"; 1996; *Cytotechnology*; vol. 21; pp. 95-109.

Rasmussen, B. et al.; "Isolation, Characterization and Recombinant Protein Expression in Veggie-CHO: A Serum-Free CHO Host Cell Line"; 1998; *Cytotechnology*; vol. 28; pp. 31-42.

Reiter, M. et al.; "Flow Cytometry and Two-Dimensional Electrophoresis (2-DE) for System Evaluation of Long Term Continuous Perused Animal Cell Cultures in Macroporous Beads"; 1992; *Cytotechnology*;.vol. 9; pp. 247-253.

Renner, W.A. et al.; "Recombinant Cyclin E Expression Activates Proliferation and Obviates Surface Attachment of Chinese Hamster Ovary (CHO) Cells in Protein-Free Medium"; Aug. 1995; *Biotechnology and Bioengineering*; vol. 47; pp. 476-482.

Ryll, T. et al.; "Production of Recombinant Human Interleukin-2 with BHK Cells in a Hollow Fibre and a Stirred Tank Reactor with Protein-Free Medium"; 1990; *Journal of Biotechnology*; vol. 14; pp. 377-392.

Scharfenberg, K. and Wagner, R.; "A Reliable Strategy for the Achievement of Cell Lines Growing in Protein-Free Medium"; 1995; *Animal Cell Technology: Developments towards the 21st Century*; pp. 619-623.

Schlaeger, E.J.; "The Protein Hydrolystate, Primatone RL, is a Cost-Effective Multiple Growth Promoter of Mammalian Cell Culture in Serum-Containing and Serum-Free Media and Displays Anti-apoptosis Properties"; 1996; *Journal of Immunological Methods*; vol. 194; pp. 191-199.

Schlokat, U. et al.; "Herstellung and Charakterisierung von rekombinantem von Willebrand-Faktor zur Therapeutischen Anwendung"; 1995; *26th Hämophilie-Symposium Hamburg*; pp. 147-158.

Schlokat, U. et al.; "Production of Highly Homogeneous and Structurally Intact Recombinant von Willebrand Factor Multimers by Furin-Mediated Propeptide Removal in vitro"; 1996; *Biotechnol. Appl. Biochem.*; vol. 24; pp. 257-267.

Schneider, Y-J.; "Optimisation of Hybridoma Cell Growth and Monoclonal Antibody Secretion in a Chemically Defined, Serum- and Protein-Free Sulture Medium"; 1989; *Journal of Immunological Methods*; vol. 116; pp. 65-77.

Sinacore, M.S. et al.; "CHO DUKX Cell Lineages Preadapted to Growth in Serum-Free Suspension Culture Enable Rapid Development of Cell Culture Processes for the Manufacture of Recombinant Proteins"; 1996; *Biotechnol. Bioeng.*; vol. 52; pp. 518-528.

Stoll, T.S. et al.; "Effects of Culture Conditions on the Production and Quality of Monoclonal IgA"; Aug. 15, 1997; *Enzyme and Microbial Technology*; vol. 21; pp. 203-211.

Sunstrom, N.-A. et al.; "Recombinant Insulin-like Growth Factor-I (IGF-I) Production in *Super*-CHO Results in the Expression of IGF-I Receptor and IGF Binding Protein 3"; 1998; *Cytotechnology*; vol. 28; pp. 91-99.

Takahashi, M. et al.; "Production of Murine Monoclonal Antibodies in Protein Free Medium"; 1997; *Animal Cell Technology: Basic & Applied Aspects*; vol. 8; pp. 167-171.

Taylor, W.G. et al.; "Studies on a Serum Substitute for Mammalian Cells in Culture. I. Biological Efficacy of Whole and Fractionated Peptone Dialysate (36086)"; 1972; *Proc. Soc. Exp. Biol. Med.*; vol. 139; pp. 96-99.

Tecce, M.F. and Terrana, B.; "High Yield and High-Degree Purification of Human α-Fetoprotein Produced by Adaptation of the Human Hepatoma Cell Line HEP G2 in a Serum-Free Medium"; 1988; *Analytical Biochemistry*; vol. 169; pp. 306-311.

Teige, M. et al.; "Problems with Serum-Free Production of Antithrombin III Regarding Proteolytic Activity and Product Quality"; 1994; *Journal of Biotechnology*; vol. 34; pp. 101-105.

Werner, R.G. et al.; "Safety and Economic Aspects of Continuous Mammalian Cell Culture"; 1992; *Journal of Biotechnology*; vol. 22; pp. 51-68.

Yamauchi, T. et al.; "Production of Human Antithrombin-III in a Serum-Free Culture of CHO Cells"; 1992; *Biosci. Biotech. Biochem.*; vol. 56(4); pp. 600-604.

Yin, Z. et al.; "Sensitivity of 3T3 Cells to Low Serum Concentration and the Association Problems of Serum Withdrawal"; 1994; *Cell Biology International*; vol. 18(1); pp. 39-46.

Zang, M. et al.; "Production of Recombinant Proteins in Chinese Hamster Ovary Cells Using a Protein-Free Cell Culture Medium"; 1995; *Biotechnology*; vol. 13; pp. 389-392.

Zang-Gandor, M.O.; "Improved Transfection of CHO Cells Using Endotoxin-Free Plasmid DNA"; *Quiagen News*; 1997; vol. 4; pp. 1, 16-18.

BD Bionutrients™; Technical Manual Advanced Bioprocessing Third Edition Revised Oct. 2006, pp. 1-67.

Deltown Specialties; Peptone Selection Guide for Diagnostic and Fermentation Nutrients, 1994, 4 pages.

Extract from Hauser, H. and Wagner, R. eds.; *Mammalian Cell Biotechnology in Protein Production*; 1997; Walter de Gruyter, Berlin; pp. 33-137.

Minutes of the Oral Proceedings to EP 99 939 251.7, 4 pages, Nov. 17, 2009.

Page from the Quest International Technical Manual on Hydrolysates, 1988.

Quest International; "Protein Derived Peptide Mixtures can Effectively Replace Serum, Glutamine and Other Free Amino Acids in Cell Culture Media"; Nov. 1998; Research Disclosure; pp. 1474-1476.

Quest International; Bioproducts Group HY-SOY®, Product Information, 1995, 1 page.

Quest International, Bioproducts Group HY SOY 2®, Product Information, 1995, 1 page.

Quest International; Bioproducts Group HY-SOY®, Product Information, 1998, 2 pages.

Quest International; Product Information; www.sheffield-products.com; accessed on Nov. 18, 2003; 14 pages.

SAFC Biosciences™, Dulbecco's Modified Eagle's Medium/Ham's Nutrient Mixture F12 Product Information, 2006, 2 pages.

SAFC Biosciences™; RPMI 1640 Medium Modified Product Information, 2006, 2 pages.

Sigma®; Biochemicals Organic Compounds Diagnostic Reagents Catalogue, 1995, 6 pages.

Sigma-Aldrich; DME/Nutrient Mixture F12 Ham Product Information, 8 pages, 2007.

AstraZeneca AB Opposition Brief to European Patent No. 1200561 dated Mar. 14, 2007.

Bayer Healthcare AG Opposition Brief to European Patent No. 1200561 dated Mar. 13, 2007.

Bioceuticals Arzneimittel AG Opposition Brief to European Patent No. 1200561 dated Mar. 14, 2007.

Biogen IDEC MA, Inc. Opposition Brief to European Patent No. 1200561 dated Mar. 14, 2007.

Campina Nederland Holding B.V. Opposition Brief to European Patent No. 1220893 dated Mar. 21, 2007.

F. Hoffmann-La Roche AG Opposition Brief to European Patent No. 1200561 dated Mar. 13, 2007.

F. Hoffmann-La Roche AG Opposition Brief to European Patent No. 1220893 dated Mar. 27, 2007.

Kerry Ingredients (UK) Limited Opposition Brief to European Patent No. 1220893 dated Mar. 21, 2007.

Maxygen Inc. Opposition Brief to European Patent No. 1200561 dated Mar. 14, 2007.

Maxygen, Inc. Opposition Brief to European Patent No. 1220893 dated Mar. 20, 2007.

Declaration of Dr. Ricardo Matanguihan in support of Maxygen, Inc. Opposition Brief to European Patent No. 1220893 dated Mar. 20, 2007 (including Annexes A and B).

Declaration of Dr. Ruediger Heidemann in support of Maxygen, Inc. Opposition Brief to European Patent No. 1220893 dated Mar. 20, 2007 (including Annexes A-F).

Merch Serono International S.A. Opposition Brief to European Patent No. 1200561 dated Mar. 12, 2007.

Merck Serono International S.A. Opposition Brief to European Patent No. 1220893 dated Mar. 20, 2007.

N.V. Organon Opposition Brief to European Patent No. 1200561 dated Mar. 14, 2007.

Novartis AG Opposition Brief to European Patent No. 1200561 dated Mar. 14, 2007.

Novartis AG Opposition Brief to European Patent No. 1220893 dated Mar. 21, 2007.

Novo Nordisk A/S Opposition Brief to European Patent No. 1200561 dated Mar. 14, 2007.

Novo Nordisk A/S Opposition Brief to European Patent No. 1220893 dated Mar. 21, 2007.

Sigma-Aldrich Co. Opposition Brief to European Patent No. 1220893 dated Mar. 21, 2007.

Wyeth Opposition Brief to European Patent No. 1200561 dated Mar. 14, 2007.

* cited by examiner

US 8,524,497 B2

ANIMAL PROTEIN FREE MEDIA FOR CULTIVATION OF CELLS

This application is a divisional of U.S. application Ser. No. 10/614,037, filed Jul. 8, 2003, which claims priority to U.S. Provisional Application No. 60/394,243, filed Jul. 9, 2002, the disclosures of each are herein incorporated by reference in their entirety.

FIELD OF THE INVENTION

The present invention relates to animal protein free cell culture media comprising a combination of a soy hydrolysate and a yeast hydrolysate. The invention also relates to animal protein free culture processes, wherein cells can be cultivated, propagated and passaged without animal proteins. These processes are useful in cultivating cells, such as recombinant cells or cells infected with a virus, and for producing biological products by cell culture processes.

BACKGROUND OF THE INVENTION

For cultivation of cells, particularly eukaryotic cells, and more specifically mammalian cells, there is a constant need to use special culture media that make available the nutrient substances and growth nutrient substances that are required for efficient growth of the cells and for the production of the proteins or viruses that are desired. Cell culture media formulations have been supplemented with a range of additives, including undefined components like fetal calf serum (FCS), several animal-derived proteins and/or protein hydrolysates of bovine origin.

In general, serum or serum derived substances, such as albumin, transferrin or insulin, may contain unwanted agents that can contaminate the cultures and the biological products obtained therefrom. Furthermore, human serum derived additives have to be tested for all known viruses, including hepatitis and HIV, that can be transmitted by serum. Moreover, bovine serum and products derived therefrom, for example trypsin, bear the risk of BSE-contamination. In addition, all serum-derived products can be contaminated by unknown agents. In the case of serum or protein additives that are derived from human or other animal sources in cell culture, numerous problems (e.g., the varying quality and composition of different batches and the risk of contamination with mycoplasma, viruses or BSE agents) exist, particularly if the cells are used for production of medicinal agents or vaccines for human administration.

Therefore, many attempts have been made to provide efficient host systems and cultivation conditions that do not require serum or other animal protein compounds. Simple serum free medium typically includes basal medium, vitamins, amino acids, organic and inorganic salts, and perhaps additional components to make the medium nutritionally complex. Such media, however, often are nutritionally insufficient and must be supplemented with animal-derived protein supplements or recombinant versions of proteins used in cell culture, such as insulin, insulin-like growth factor or other growth factors.

To avoid the use of animal protein supplements in serum free cell culture medium, several attempts have been made to provide cell culture media that are completely free of proteins.

Cinatl et al., *Cell Biology International* 17:885-895 (1993) disclose the development of a media (PFK-1) specific for continuous propagation of VERO cells on a polyvinyl formal (PVF) culture surface.

WO 96/15231 discloses serum-free medium composed of a synthetic minimal essential medium and yeast extract for propagation of vertebrate cells and virus production process.

A medium formulation composed of a basal cell culture medium comprising a rice peptide and an extract of yeast or an enzymatic digest thereof, and/or a plant lipid for growth of animal cells is disclosed in WO 98/15614.

A medium comprising purified soy hydrolysate for the cultivation of recombinant cells is disclosed in WO 01/23527.

WO 00/03000 discloses a medium that comprises a soy hydrolysate and a yeast extract, but also requires the presence of recombinant forms of animal proteins, such as growth factors.

For efficient production of biological products, such as viruses or recombinant proteins, it is important that optimal cell density is reached to obtain maximal product yield.

Therefore, a current need exists to increase growth, metabolic activity and density of cells, and to provide optimal cell culture medium devoid of animal proteins for production of biological products, such as those used as medicinals or vaccines in humans. Furthermore, the down-stream processing, e.g. purification of the desired product from culture medium can be more cost-effective and time-efficient if animal proteins are not present in the medium. Additionally, unwanted immunogenic animal proteins may induce deleterious immunological reactions, which are avoided with practice of the present invention.

BRIEF SUMMARY OF THE INVENTION

It is an object of the present invention to provide animal protein free culture media. In accomplishing this and other objects, there is provided, in accordance with one aspect of the invention, an animal protein free cell culture medium comprising soy hydrolysate and yeast hydrolysate. The soy hydrolysate can be present in a concentration of at least 0.05% (w/v) and yeast hydrolysate is present in a concentration of at least 0.05% (w/v). Optionally, the soy hydrolysate can be present in a concentration of less than 1.0% (w/v) and yeast hydrolysate can be present in a concentration of less than 0.3% (w/v). Optionally, the soy hydrolysate can be present in a concentration of between about 0.2% (w/v) to about 0.6% (w/v) and yeast hydrolysate can be present in a concentration of between about 0.05% (w/v) to about 0.2% (w/v). Optionally, the soy hydrolysate can be present in a concentration of between about 0.25% (w/v) to about 0.35% (w/v) and the yeast hydrolysate can be present in a concentration of between about 0.05% (w/v) to about 0.15% (w/v). Optionally, the soy hydrolysate can be present in a concentration of about 0.3% (w/v) and the yeast hydrolysate can be present in a concentration of about 0.1% (w/v). Optionally, the medium comprises 3 parts by weight soy hydrolysate to 1 part by weight yeast hydrolysate. The yeast hydrolysate can be a ultrafiltrated purified yeast hydrolysate, wherein at least 40% of said yeast hydrolysate has a molecular weight of less than or equal to 500 Daltons. Similarly, the soy hydrolysate can be a ultrafiltrated purified soy hydrolysate, wherein at least 40% of said soy hydrolysate has a molecular weight of less than or equal to 500 Daltons.

The invention also provides methods of cultivating cultures of cells comprising providing a medium comprising soy hydrolysate at a concentration of about 0.05% (w/v) to about 1% (w/v) and yeast hydrolysate at a concentration of about 0.05% (w/v) to about 0.3% (w/v); and propagating the cells in the medium to form the cell culture. Other concentrations of hydrolysates, as exemplified above, also can be employed according to the invention. The cells can be animal cells, such as insect cells, avian cells, mammalian cells, stem cells, and preferably those cells that are used for in vitro virus production. The cells also can be recombinant cells. Exemplary cells include those selected from the group of cells consisting of BSC-1 cells, LLC-MK cells, CV-1 cells, COS-cells, VERO cells, MDBK cells, MDCK cells, CRFK cells, RAF cells, RK-cells, TCMK-1 cells, LLC-PK cells, PK15 cells, LLC-RK cells, MDOK cells, BHK-21 cells, CHO cells, NS-1 cells MRC-5 cells, WI-38 cells, BHK cells, 293 cells and RK-cells.

The invention also provides an animal protein free confluent cell culture process, comprising: providing an animal protein free medium comprising soy hydrolysate and yeast hydrolysate; growing the cells in the medium, and passaging and sub-cultivating the cells grown in the medium while in contact with a non-animal-derived protease in order to obtain a confluent cell culture. The cells can be animal cells, recombinant cells and/or cells infected with a virus. The media characteristics and cell types set forth herein are applicable here as well.

Moreover, the invention provides a culture of cells cultivated in an animal protein free medium, wherein the medium comprises soy hydrolysate at a concentration of about 0.05% (w/v) to about 1% (w/v) and yeast hydrolysate at a concentration of about 0.05% (w/v) to about 0.3% (w/v). Other concentrations of hydrolysates, as exemplified above, also can be employed according to the invention. The cells can be animal cells, recombinant cells and/or cells infected with a virus. The media characteristics and cell types set forth herein are applicable here as well.

Additionally, the invention provides methods for producing viruses, comprising: providing a culture of cells that have been grown in an animal protein free medium comprising soy hydrolysate and a yeast hydrolysate; infecting the cells with a virus; and incubating the infected cells to propagate the virus. The cells can be animal cells and/or recombinant cells and, in particular, mammalian cells. The media characteristics and cell types set forth herein are applicable here as well. The viruses to be produced on the cultured cells may be chosen from the range of viruses known to infect the cultured cell type. For instance, when utilizing a mammalian cell culture, viruses may be chosen from the genera of orthomyxoviruses, paramyxoviruses, reoviruses, picornaviruses, flaviviruses, arenaviruses, herpesviruses, poxviruses, coronaviruses and adenoviruses. The virus used may be a wild-type virus, an attenuated virus, a reassortant virus, or a recombinant virus. In addition, instead of actual virions being used to infect the cells with a virus, an infectious nucleic acid clone may be utilized according to infectious clone transfection methods known to those of skill in the field of virology.

The invention further provides methods for producing poxviruses (including vaccinia virus), comprising: providing a culture of cells that have been grown in an animal protein free medium comprising soy hydrolysate and yeast hydrolysate; infecting the cells with poxvirus; and incubating the infected cells to propagate poxvirus. The cells can be mammalian cells and/or recombinant cells. The media characteristics and cell types set forth herein are applicable here as well.

Furthermore, the invention further provides methods for producing coronaviruses (including the Severe Acute Respiratory Syndrome associated coronavirus), comprising: providing a culture of cells that have been grown in an animal protein free medium comprising soy hydrolysate and yeast hydrolysate; infecting the cells with coronavirus; and incubating the infected cells to propagate coronavirus. The cells can be mammalian cells and/or recombinant cells. The media characteristics and cell types set forth herein are applicable here as well.

Furthermore, the invention provides methods for producing orthomyxoviruses, comprising: providing a culture of cells that have been grown in an animal protein free medium comprising soy hydrolysate and yeast hydrolysate; infecting the cells with orthomyxovirus; and incubating the infected cells to propagate orthomyxovirus. The orthomyxovirus can be Influenza A, B or C virus. The cells can be mammalian cells and/or recombinant cells. The media characteristics and cell types set forth herein are applicable here as well.

The invention additionally provides methods for producing Ross River virus, comprising providing a culture of cells that have been grown in an animal protein free medium comprising soy hydrolysate and yeast hydrolysate; infecting the cells with Ross River virus; and incubating the infected cells to propagate Ross River virus. The cells can be mammalian cells and/or recombinant cells. The media characteristics and cell types set forth herein are applicable here as well.

The invention also provides methods for producing Flavivirus, comprising providing a culture of cells that have been grown in an animal protein free medium comprising soy hydrolysate and yeast hydrolysate; infecting the cells with Flavivirus; and incubating the infected cells to propagate Flavivirus. The Flavivirus can be selected from the group consisting of Yellow fever virus, and chimeric viruses derived therefrom, Japanese encephalitis virus, Tick-borne encephalitis virus, West nile Virus and Hepatitis C virus. The cells can be animal cells and/or recombinant cells. The media characteristics and cell types set forth herein are applicable here as well.

The invention further provides methods of producing immunogenic compositions comprising a viruses or a virus antigens, wherein the method comprises providing a culture of cells that have been grown in an animal protein free medium comprising soy hydrolysate and yeast hydrolysate; infecting the cells with the virus; incubating the infected cells to propagate the virus; harvesting the virus or virus antigen produced; preparing an immunogenic composition from the harvested virus or virus antigen. The cells can be animal cells and/or recombinant cells. The media characteristics and cell types set forth herein are applicable here as well. The harvested virus or virus antigen can be subjected to purification.

The invention also provides methods of producing immunogenic compositions comprising a virus or a virus antigen, wherein the method comprises: providing a culture of mammalian cells, wherein the cells are selected from the group of monkey kidney cells, bovine kidney cells, dog kidney cells, pig kidney cells, mouse kidney cells, rat kidney cells, sheep kidney cells, hamster kidney cells and human cells that have been grown in an animal protein free culture medium comprising a soy hydrolysate and a yeast hydrolysate; infecting the cells with a virus selected from the group of orthomyxoviruses, paramyxoviruses, reoviruses, picornaviruses, flaviviruses, arenaviruses, herpesviruses, poxviruses, coronaviruses and adenoviruses; incubating the culture of cells to propagate the virus; harvesting the virus or virus antigen so produced; and preparing an immunogenic composition from the harvested virus or virus antigen.

Additionally, the invention provides cultures of cells infected with orthomyxovirus, poxvirus, paramyxovirus, reovirus, picornavirus, flavivirus, arenavirus, herpesvirus, poxvirus or adenovirus, wherein the cells are cultivated in an animal protein free medium, wherein the medium comprises soy hydrolysate and yeast hydrolysate. The soy hydrolysate can be a concentration of about 0.05% (w/v) to about 1% (w/v) and the yeast hydrolysate can be at a concentration of about 0.05% (w/v) to about 0.3% (w/v). Other concentrations of hydrolysates, as exemplified above, also can be employed according to the invention.

The invention further provides preparations of orthomyxovirus, paramyxovirus, reovirus, picornavirus, flavivirus, arenavirus, herpesvirus, poxvirus, coronavirus or adenovirus that are free of animal proteins, including recombinantly-produced versions thereof, from the media, wherein the preparation is obtainable by cultivating cells infected with influenza virus in an animal protein free medium, wherein the medium comprises soy hydrolysate and yeast hydrolysate. The soy hydrolysate can be a concentration of about 0.05% (w/v) to about 1% (w/v) and the yeast hydrolysate can be at a concentration of about 0.05% (w/v) to about 0.3% (w/v). Other concentrations of hydrolysates, as exemplified above, also can be employed according to the invention. These viral preparations are suitable for use to make viral antigen and vaccines after further processing.

These and other aspects of the invention will become apparent to the skilled person in view of the explanation and data set forth below.

DETAILED DESCRIPTION OF THE INVENTION

The term "animal protein free medium," in its various grammatical forms, refers to a medium that is not supplemented with proteins and protein components from higher multicellular non-plant eukaryotes (that is, vertebrates), that possess the secondary, tertiary and quaternary structures characteristic of the proteins as they occur in nature. Typical proteins that are avoided are those found in serum and serum derived substances, such as albumin, transferrin, insulin and other growth factors. Recombinantly-produced versions of animal proteins, which can contain immunogenic bacterial components, also are avoided according to the invention, and are not present in the animal protein free medium of the invention. Animal proteins and protein components are to be distinguished from non-animal proteins, small polypeptides and oligopeptides obtainable from plants (usually about 10-30 amino acids in length), such as the soy bean, and lower eukaryotes, such as yeast. Of course, once the media is contacted or inoculated with the cells to be propagated, the media will contain animal proteins shedded or secreted by those cells, including any recombinant proteins expressed by genetically modified cells if such cells are cultivated. Thus, the term animal protein free medium, and biological materials and preparations produced therewith, is not to be construed to require the absence of proteins shedded or secreted by cells propagated in the media, but rather refers to a lack of direct supplementation of media with animal proteins and protein components obtained from animal sources or the like produced recombinantly.

The term "basal medium," in its various grammatical forms, is a synthetic medium, such as DMEM, HAM's F12, Medium 199 or RPMI, or combinations thereof, and others that are known from the literature or are commercially available. In accordance with the invention, every synthetic medium, that does not contain animal proteins, can be used in combination with the soy hydrolysate and yeast hydrolysate combination. The basal medium can comprise a number of ingredients, including amino acids, vitamins, organic and inorganic salts, sources of carbohydrate, each ingredient being present in an amount which supports the cultivation of a cell in vitro. For example, DMEM/HAM's F12 (1:1) medium as basal medium can be used. The medium may contain auxiliary substances, such as buffer substances like sodium bicarbonate, oxidation stabilizers, stabilizers to counteract mechanical stress, or protease inhibitors. If required, a nonionic surfactant, such as polypropylene glycol (PLURONIC F-61, PLURONIC F-68, SYNPERONIC F-68, PLURONIC F-71 or PLURONIC F-108) can be added to the medium as a defoaming agent. These agents are generally used to protect cells from the negative effects of aeration since, without an addition of a surfactant, the ascending and bursting air bubbles can lead to damage of those cells that are located on the surface of these air bubbles ("sparging"). The quantity of nonionic surfactant is preferably between about 0.05 and about 10 g/L, typically between about 0.1 and about 5 g/L. In addition, the medium also can contain cyclodextrin or derivatives thereof, typically between about 0.001 g/L and about 1 g/L.

According to the invention, the medium comprises soy hydrolysate and yeast hydrolysate, which can be added to a basal medium. The term "hydrolysate" includes an enzymatic digest of soy peptone or yeast extract. The hydrolysate can be obtained from a plurality of soy peptone or yeast extract preparations, respectively, which can be further enzymatically digested (for example, by papain), and/or formed by autolysis, thermolysis and/or plasmolysis. Hydrolysates also may be obtained commercially, such as Hy-Soy, Hy-Yeast 412 and Hi-Yeast 444, from sources such as Quest International, Norwich, New York, OrganoTechnie, S.A. France; or Deutsche Hefewerke GmbH, Germany. Sources of yeast extracts also are disclosed in WO 98/15614. Sources of yeast extracts and soy hydrolysates also are disclosed in WO 00/03000.

The hydrolysates used in media of the invention are preferably purified from a crude fraction, because impurities which could interfere with efficient cultivation are preferably eliminated during this purification, thereby improving the consistency of the hydrolysate. Purification can be by ultrafiltration or Sephadex chromatography, for example, with Sephadex G25 or Sephadex G10 or equivalent materials, ion-exchange chromatography, affinity chromatography, size exclusion chromatography or "reversed-phase" chromatography. These processes are known in the field. Using these methods, fractions can be selected which contain soy or yeast hydrolysate of defined molecular weight, preferably $\leqq 1000$ Daltons, more preferably $\leqq 500$ Daltons, still more preferably $\leqq 350$ Daltons. At least 90% of the hydrolysate is preferably of a molecular weight of $\leqq 1000$ Dalton. The average molecular weights of the soy and yeast hydrolysates are preferably between about 220 and 375 daltons. The pH value of the soy hydrolysate and the yeast hydrolysate should be in the range between about 6.5 and 7.5. The total nitrogen content should be about between 8 and 11%, preferably, between 9.0 and 10.0% and the ash content $\leqq 18\%$. An advantageous hydrolysate is characterized by the feature that it has a free amino acids content of between about 5 and 30%. Endotoxin content, if any, should be <500 U/g.

One medium according to the invention has the following constituency: synthetic minimal medium (DMEM/HAM's F12 (1:1) medium (1-25 g/L), soy hydrolysate (0.5-10 g/L) and yeast hydrolysate (0.5-3 g/L), L-glutamine (0.05-1 g/L), NaHCO$_3$ (0.1-10 g/L). The pH of the medium is between pH 6.8 and 7.6, preferably between pH 7.0 and 7.3.

As is apparent to the skilled person, the term "about" in the context of numerical values and ranges refers to values or ranges that approximate or are close to the recited values or ranges such that the invention can perform as intended, such as having promoting a desired degree of cell growth, as is apparent from the teachings contained herein, and applies to all values. Thus, this term encompasses values beyond those resulting from systematic error.

It has been surprisingly found that an animal protein free basal medium supplemented with yeast hydrolysate and soy hydrolysate within the range according to the present invention is more favorable for cell growth rate, cell metabolic activity and final cell density as compared to the medias described in the prior art. This was even more surprising in view of the teaching of WO 98/15614 showing that higher plant peptide concentrations are less optimal. With an animal protein free medium of the invention comprising yeast hydrolysate and soy hydrolysate as described herein, cells showed higher growth rate, higher final cell density of the biomass and increased metabolic activity (expressed in oxygen consumption in % per min) compared to medium either comprising soy hydrolysate or yeast hydrolysate alone, even if the final concentration of yeast hydrolysate or soy hydrolysate solely added to the medium is equivalent to the sum of the combined hydrolysate concentration. For example, a final concentration of about 0.4% (w/v) yeast hydrolysate in the medium alone had an inhibitory effect on cell growth and cell density. A medium comprising 0.4% (w/v) or higher concentrations of soy hydrolysate reached no higher cell density than a medium comprising 0.3% (w/v). However, a medium comprising a combination of soy hydrolysate and yeast hydrolysate in a final total hydrolysate concentration of 0.4% (w/v) showed a significant increase in cell metabolic activity, cell growth and final cell density.

In accordance with the invention, the sum of the amount of the soy and yeast hydrolysate in the medium should be between about 0.2% (w/v) and about 0.6% (w/v) with a higher ratio of soy hydrolysate in the medium compared to yeast hydrolysate. An optimal ratio between soy and yeast hydrolysate should be about 3:1 (soy/yeast), respectively.

The media of the invention as described herein is in particular useful to cultivate cells. Within the scope of the invention, the term "cells" means a generic term and encompass the cultivation of individual cells, tissues, organs, insect cells, avian cells, mammalian cells, primary cells, continuous cell lines, stem cells and/or genetically engineered cells, such as recombinant cells expressing a hetereologous polypeptide or protein. Recombinant cells include, for example, CHO cells or BHK cells expressing heterologous polypeptides or proteins, such as a growth factor or a blood factor. Cells often used for the propagation of virus include VERO cells and CV-1 cells.

Mammalian cells suitable for cultivation in the cell culture medium of the present invention include those of human origin, which may be primary cells derived from a tissue sample, diploid cell strains, transformed cells or established cell lines. Mammalian cells can include human and non-human cells alike. Mammalian cells of non-human origin can be monkey kidney cells, bovine kidney cells, dog kidney cells, pig kidney cells, rabbit kidney cells, mouse kidney cells, rat kidney cells, sheep kidney cells, hamster kidney cells, Chinese hamster ovarian cells or an animal cell derived from any tissue. In particular, mammalian cells that can cultivated in the culture medium can be BSC-1 cells, LLC-MK cells, CV-1 cells, COS-cells, COS-1 cells, COS-3 cells, COS-7 cells, VERO cells, MDBK cells, MDCK cells, CRFK cells, RAF cells, RK-cells, TCMK-1 cells, LLC-PK cells, PK15 cells, LLC-RK cells, MDOK cells, BHK-21 cells, CHO cells, 293 cells, NS-1 cells MRC-5 cells, WI-38 cells, BHK cells, 293 cells and RK-cells. Examples or recombinant cells include CHO cells expressing Factor VIII, FII, FIX, FX, vWF, for example, all of which are known to the person skilled in the art.

The terms "continuous cells" or "continuous cell line" (CCL), in their various grammatical forms, mean cultured cells that replicate indefinitely and are capable of growing in suspension culture or large scale cultivation in bioreactor. The unrestricted growth of CCLs permits long-term cultivation from a standardized cell substrate and low costs. Mammalian cell lines can be selected from the group of CHO cells, COS cells, VERO cells, LLK-MK2 cells, NS-1 cells, MDBK cells, MDCK cells, MRC-5 cells, WI-38 cells, BHK cells, CV-1 cells, rabbit kidney (RK) cells and other cell lines as disclosed by Butler et al. BIOS Scientific Publisher p. 1-24 (1992), which is incorporated herein by reference. The CCLs are preferably tested for absence of adventitious agents, such as bacteria, fungi, mycoplasma, protozoans and viruses.

The term "cell culture," in its various grammatical forms, refers to cells grown in suspension, roller bottles, flasks and the like. Large scale approaches, such as bioreactors, including adherent cells growing attached to microcarriers in stirred fermentors, also are included. Moreover, it is possible to not only to culture surface-dependent cells, but also to use the suspension culture techniques with the inventive media. If the cells are grown on microcarriers, the microcarrier can be selected from the group of microcarriers based on dextran, collagen, plastic, gelatin and cellulose and others as described in Butler, Spier & Griffiths, Animal cell Biotechnology 3:283-303 (1988). Porous carriers, such as e.g. Cytoline® or Cytopore®, as well as dextran-based carriers, such as DEAE-dextran (Cytodex 1®), quaternary amine-coated dextran (Cytodex 2®) or gelatin-based carriers, such as gelatin-coated dextran (Cytodex 3®) are suitable. These carriers can be obtained from Pharmacia.

The cells are preferably grown from the ampoule to the biomass in the animal protein free media and kept under culture medium conditions during cell culture growth and product production process. Cells that have already been adapted to the media are preferably used. It has been found that not only increased yields be achieved with such pre-adapted cells, but their stability for cultivation also is clearly improved by the use of the medium in accordance with the invention.

The term "cultivation," in its various grammatical forms, refers to the maintenance of the cells in vitro under conditions permissive for growth and continued viability. Mammalian cells are typically cultivated in a cell incubator at about 37° C., with the culture medium having an optimal pH in the range of about 6.8 to 7.6, preferably between 7.0 and 7.3. Cells in batch culture might have a complete medium change about every 2 to 3 days, or more or less frequently, if required. Cells in perfusion culture (e.g. in bioreactor or fermenter) might have a fresh media change on a continuously recirculating basis. Cultivation approaches can include, depending on context and need, the sub-cultivation, passaging and propagation of the cells.

The invention thus provides methods for cultivating cells comprising the steps of growing cells in a basal medium comprising yeast hydrolysate and soy hydrolysate. Preferably the cells are grown in a medium comprising soy hydrolysate in a concentration of 0.05% (w/v) to 1.0% (w/v) and yeast hydrolysate in a concentration of 0.05% (w/v) to 0.3% (w/v). According to this aspect of the invention, the cells are grown from small scale to large scale biomass in animal protein free media of the invention. The passaging and subcultivation of the cells to obtain a cell culture biomass is preferably performed with a non-animal-derived protease, such as Pronase or a purified fraction thereof. One protease is the purified trypsin-like fraction of *Streptomyces griseus* (SGT) as described in U.S. application Ser. No. 10/006,223, the entirety of which is hereby incorporated by reference. To avoid animal-derived material during cultivation of a cell culture, in particular during cultivation of adherent cells that grow attached to a carrier, the carrier is preferably a synthetic carrier, or a microcarrier coated with a non-animal derived material. For example a DEAE-dextran or quaternary amine-coated dextran microcarrier.

The invention also provides an animal protein free cell culture process, wherein cells are cultivated, sub-cultivated and passaged under conditions devoid of animal proteins. The process comprising the steps of providing an animal protein free medium comprising yeast hydrolysate and soy hydrolysate, growing cells in said medium, passaging and sub-cultivating said cells grown in that medium using a non-animal-derived protease, further growing the sub-cultivated cells to reach a confluent cell density and repeating the steps of sub-cultivation and growth of cells until the final cell culture biomass desired is reached. The process includes the growth of the cells in animal protein free medium, sub-cultivating and passaging the cells using a non-animal derived protease, preferably a purified trypsin-like fraction of *Streptomyces griseus* (SGT). During cultivation of adherent cells that grow attached to a carrier, the carrier is preferably a synthetic carrier, or a microcarrier coated with a non-animal derived material. By the combination of these steps the use of animal proteins can be avoided.

Cells suitable for growth in the animal protein free media of the present invention include, but are not limited to, BSC-1 cells, LLC-MK cells, CV-1 cells, VERO cells, MDBK cells, MDCK cells, CRFK cells, RAF cells, TCMK-1 cells, LLC-PK cells, PK15 cells, LLC-RK cells, MDOK cells, RK-cells, BHK-21 cells, WI-38 cells, 293 cells and/or MRC-5 cells. These cells can be infected with viruses, such as an orthomyxovirus, paramyxovirus, reovirus, picornavirus, flavivirus, arenavirus, herpesvirus, poxvirus, coronavirus, adenovirus and other viruses known to the skilled person. More specifically, the virus used to infect the cell culture can be Influenza virus, vaccinia virus and variola, fowlpox virus, cowpox virus, tick-borne encephalitis virus (TBE), poliovirus, Hepatitis A Virus, Ross River Virus, Yellow fever virus and a chimeric virus derived thereof, West nile virus, Japanese encephalitis virus, rubella virus, hepatitis C virus (HCV), mumps virus, measles virus, respiratory syncytial virus (RSV), herpes simplex virus (HSV), cytomegalovirus (CMV), Epstein-Barr virus (EBV), rotavirus, foot and mouth disease virus (FMDV). It is within the knowledge of the skilled in the art to select the virus and the cells for which the virus is can be propagated. The cells can be cultivated in the media of the invention and grown to reach an optimal cell density prior infection with the respective virus. Surprisingly, a cell culture grown and propagated in an animal protein free medium of the invention shows a significant increase of virus yield productivity. Examples of different viruses propagated on cells cultivated and grown of the medium of the invention have shown a 2 to 5 fold increase of virus yield compared to a medium comprising solely yeast extract. This makes the system more favorable for cell growth and virus production processes than the those described in the prior art.

According to an embodiment of the invention, the cells are VERO cells and the virus is selected from the group of Influenza Virus, TBE-Virus, vaccinia virus, poliovirus, Hepatitis A Virus, Ross River Virus, Yellow fever virus and a chimeric virus derived thereof, West nile virus, Japanese encephalitis virus, rubella virus, HCV, mumps virus, measles virus, respiratory syncytial virus, HSV, CMV, EBV, rotavirus. Other viruses known to grow in VERO cells also can be used.

The invention also provides for production of vaccinia virus by providing a culture of cells grown and cultivated in an animal protein free medium comprising yeast hydrolysate and soy hydrolysate, infecting said cells with a vaccinia virus and incubating the culture of cells to propagate the vaccinia virus. Preferably, the cells are grown in a medium comprising soy hydrolysate in a concentration of about 0.05% (w/v) to about 1.0% (w/v) and yeast hydrolysate concentration of about 0.05% (w/v) to about 0.3% (w/v). According to this aspect of the invention the cells can VERO cells, CV-1 cells, RK-cells, BHK-21 cells, MRC-5 cells, or any cell to which vaccinia virus can be grown. The vaccinia virus can be a naturally-occurring vaccinia virus, smallpox virus vaccine strain, virulent vaccinia strains, attenuated vaccinia strains and a recombinant vaccinia viruses.

Also provided is production of orthomyxovirus by providing a culture of cells cultivated and grown in an animal protein free medium made from a basal medium comprising yeast hydrolysate and soy hydrolysate, infecting the cells with a orthomyxovirus and incubating the culture of cells to propagate the orthomyxovirus. Preferably, the cells are grown in a medium comprising soy hydrolysate in a concentration of about 0.05% (w/v) to about 1.0% (w/v) and yeast hydrolysate in a concentration of about 0.05% (w/v) to about 0.3% (w/v). The cells can be BSC-1 cells, CV-1 cells, VERO cells, MDBK cells, MDCK cells, MDOK cells, BHK-21 cells, WI-38 cells, MRC-5 cells or any cell to which orthomyxovirus can be propagated. The orthomyxovirus can be a Influenza virus, such as Influenza A, B or C.

There also is provided production of Ross River Virus by providing a culture of cells grown and cultivated in an animal protein free medium made from a basal medium comprising yeast hydrolysate and soy hydrolysate, infecting said cells with a Ross River Virus and incubating the culture of cells to propagate the Ross River Virus. Preferably, the cells are grown in a medium comprising soy hydrolysate at a concentration of about 0.05% (w/v) to about 1.0% (w/v) and yeast hydrolysate at a concentration of about 0.05% (w/v) to about 0.3% (w/v). The cells can be BSC-1 cells, CV-1 cells, VERO cells, MDBK cells, MDCK cells, CRFK cells, BHK-21 cells, WI-38 cells, MRC-5 cells or any cell to which Ross River Virus can be propagated.

Additionally, there is provided production of Flavivirus by providing a culture of cells grown and cultivated on an animal protein free medium made from a basal medium comprising yeast hydrolysate and soy hydrolysate, infecting the cells with a Flavivirus and incubating the culture of cells to propagate the Flavivirus. Preferably, the cells are grown in a medium comprising soy hydrolysate in a concentration of about 0.05% (w/v) to about 1.0% (w/v) and yeast hydrolysate in a concentration of about 0.05% (w/v) to about 0.3% (w/v). The Flavivirus can be a Yellow fever virus, or a recombinant of chimeric derivatives thereof, Japanese encephalitis virus, Tick-borne encephalitis virus, West nile Virus, and Hepatitis C virus. The cells types identified herein can be used for the propagation of flavivirus.

There is provided production of Picornavirus by providing a culture of cells grown and cultivated on an animal protein free medium made from a basal medium comprising yeast hydrolysate and soy hydrolysate, infecting the cells with a Picornavirus and incubating the culture of cells to propagate the Picornavirus. Preferably, the cells are grown in a medium comprising soy hydrolysate in a concentration of about 0.05% (w/v) to about 1.0% (w/v) and yeast hydrolysate in a concentration of about 0.05% (w/v) to about 0.3% (w/v). The Picornavirus can be a poliovirus or hepatitis A virus. The cells types identified herein can be used for the propagation of Picornavirus.

The invention also provides methods of producing immunogenic compositions comprising a virus or a virus antigen comprising the steps of providing a culture of animal cells, wherein the cells are selected from the group of monkey kidney cells, bovine kidney cells, dog kidney cells, pig kidney cells, mouse kidney cells, rat kidney cells, sheep kidney cells, rabbit kidney cells, hamster kidney cells and human cells that have been grown the a medium of the invention; infecting the cells with a virus selected from the group of orthomyxoviruses, paramyxoviruses, reoviruses, picornaviruses, flaviviruses, arenaviruses, herpesviruses, poxviruses, coronaviruses and adenoviruses, incubating the culture of cells to propagate the virus, harvesting the virus produced and preparing an immunogenic composition from the virus harvested. The virus produced and harvested can be purified with a method known in the art, such as ion exchange or gel filtration.

Having now generally described this invention, the same will be further understood by reference to the following examples which are provided herein for purposes of illustration and are not limiting in any manner.

EXAMPLES

Example 1

Formulation of the Culture Medium

Animal protein free medium is prepared with a basal DMEM/HAM's F12 (1:1) medium that is supplemented with inorganic salts, amino acids, vitamins and other components. Also added are sodium bicarbonate (1-3 g/L), L-Glutamine (0.1 to 1 g/L) and varying concentrations of soy hydrolysate (Quest Technologies, New York) or yeast hydrolysate (Deutsche Hefewerke, Germany) or combinations thereof.

Example 2

Propagation of Cells in Animal Protein Free Medium
VERO Cells in Animal Protein Free Medium VERO cells (African Green Monkey, Cercopthecus aethiops, kidney) were used as cell line. The cells have been obtained from the American Type Cell Culture Collection, Rockville, Maryland at a passage number 124 under the designation ATCC CCL 81. The cells were grown in various media as described herein.

Cells of the working cell bank were expanded in T-flasks and roller bottles and microcarrier systems with a split ratio 1:6-1:8. The cells were grown at 37° C. for 6-8 days. The culture conditions of oxygen saturation 20%+/−10% and pH 7.1+/−0.35 were kept constant. At the end of biomass production when cell have reached confluence growth, the cell density and oxygen consumption rate was determined.

The cell number of the biomass of the cell culture at the end of biomass production was determined either by trypsinization of the cells and counting with a CASY® cell counter (method A) as described by Schärfe et al. *Biotechnologie in LaborPraxis* 10:1096-1103 1988) or by citric acid and crystal violet treatment followed by counting with a haemocytometer (method B) as described by Sanford et at, *J. Nat'l Cancer Inst.* 11:773-795 (1951).

VERO cells were cultivated and grown in animal protein free medium comprising yeast hydrolysate in a concentration of 0.05%, 0.1%, 0.2%, 0.3% or 0.4%, 0.5% (w/v), or soy hydrolysate in a concentration of 0.05%, 0.1%, 0.2%, 0.3% or 0.4%, 0.5% (w/v), or soy hydrolysate and yeast hydrolysate in a concentration of yeast to soy (yeast/soy) of 0.05%/0.05% (w/v), 0.1%/0.2% (w/v), 0.1%/0.3% (w/v), 0.2%/0.2% (w/v), 0.3%/0.2% (w/v) or 0.2%/1.0% (w/v). The cell density of the cell culture at the end of biomass production in animal protein free medium comprising varying concentrations of soy hydrolysate, yeast hydrolysate or combinations thereof was calculated by methods A and B.

The results demonstrate that yeast and soy hydrolysate alone supported cell growth. At a concentration of 0.1% yeast hydrolysate a cell density of about $11.8 \times 10^5$ cells/ml was reached, however increasing concentration of yeast hydrolysate to higher than 0.3% (w/v) had a negative effect on cell growth and consequently on cell density. Concentrations of soy hydrolysate alone between 0.1% (w/v) to 0.2% (w/v) showed less cell growth and cell density than with soy concentrations of 0.3% (w/v) and 0.4% (w/v). Nevertheless, cell density and oxygen consumption of cells cultivated in medium comprising 0.3% (w/v) or 0.4% (w/v) soy hydrolysate did not differ significantly and higher concentrations to about 1% w/v of soy hydrolysate had no positive effect on cell growth. The optimal concentration of soy hydrolysate alone was determined to be between 0.2% w/v to 1.0% w/v. By supplementation of the basal medium with a combination of soy hydrolysate and yeast hydrolysate the final cell density reached was significantly increased compared to a medium comprising solely soy or yeast hydrolysate. The cell density reached at a concentration of 0.05% (w/v) soy and 0.05% (w/v) yeast was about $12.1 \times 10^5$ cells/ml and had a higher cell culture cell density compared to cells grown in medium comprising solely either 0.1% (w/v) soy hydrolysate ($10 \times 10^5$ cells/ml) or 0.1% (w/v) yeast hydrolysate ($11.8 \times 10^5$ cells/ml). The cell density of a cell culture grown in a medium comprising yeast with a concentration of 0.2% (w/v) and soy of 1.0% (w/v) was similar to the density obtained in medium comprising 0.05% (w/v) soy and 0.05% yeast (w/v).

The most significant effect on cell growth was in medium wherein the soy hydrolysate concentration compared to yeast hydrolysate was about 2-3 times higher. Cells grown in a medium comprising soy hydrolysate at concentration of about 0.3% (w/v) and yeast hydrolysate of about 0.1% (w/v) reached a cells density of about $21.0 \times 10^5$ cells/ml and showed therefore an approximately 2 times higher cell density compared to cells grown solely in soy hydrolysate of about 0.4% (w/v) and an about 2.5 times higher cells density compared to cells cultivated in medium comprising solely yeast hydrolysate of about 0.4% (w/v). The metabolic activity of cells cultivated in medium comprising yeast and soy hydrolysate also was higher compared to cells grown in medium solely comprising yeast or soy hydrolysate. The oxygen consumption rate was 1.5 (% per min.) in a medium comprising 0.1% (w/v) yeast hydrolysate and less than 1.0 (% per min.) in medium comprising 0.4% (w/v) yeast hydrolysate or soy hydrolysate alone. In a medium comprising 0.1% (w/v) yeast hydrolysate and 0.3% (w/v) soy hydrolysate the oxygen consumption was about 2.9 (% per min.), which was about 2 times higher than of cells cultivated in a medium comprising solely soy or yeast hydrolysate.

Additionally the cell cycle, which is 7 days in animal protein free medium supplemented with yeast or soy hydrolysate alone, is reduced to 6 days in the hydrolysate combination (soy and yeast) medium.

Example 3

Propagation of Recombinant Cells

A cell culture of recombinant mammalian cells, such as rFVIII-CHO cells, are cultivated in a 10 L stirred tank with perfusion. A medium in accordance with Example 1 is used as cultivation and growth medium. The cells are immobilized on a porous microcarrier (Cytopore®, Pharmacia) and cultivated for at least 6 weeks. The perfusion rate is 4 volume changes per day; the pH is 6.9 to 7.2; the $O_2$ concentration is approximately 20-50% and the temperature is 37° C. The cell density is determined.

Example 4

Comparison of Virus Antigen Production on VERO Cells Grown in Medium Supplemented with Yeast Hydrolysate and Soy Hydrolysate a. Production of Cell Culture Biomass VERO cells with a defined passage number were thawed from liquid nitrogen and passaged in roux and roller bottles to produce sufficient cells to inoculate a 1.5 liter bioreactor. Cells are either grown in basal medium supplemented either with yeast hydrolysate or with a combination of yeast hydrolysate and soy hydrolysate as described in Examples 1 and 2. After reaching confluency with a final cell density of $1.5 \times 10^6$ cells/ml, the cells were released from the microcarrier with a purified fraction of Pronase, the *S. griseus* trypsin (SGT) as described in U.S. application Ser. No. 10/006,223 and transferred to a 10 liter bioreactor. This in turn was used as an inoculum for a 100 liter bioreactor having a microcarrier concentration of 3.0 g/l. Starting from a working cell bank ampoule containing $10^7$ cells, about 30 generations were needed to reach the final confluent VERO cell biomass in the last fermenter vessel. The cells were grown at 37° C. The culture conditions of oxygen saturation 20% +/−10% and pH 7.1+/−0.35 were kept constant during virus propagation process.

Cells of the working cell bank of VERO cells were expanded in T-flasks and roller bottles with a split ratio of 1:6. Further propagation of the cells was performed in 1.5, 10 and a 50 l stirred fermenter as bioreactor using Cytodex1® microcarrier as attachment substrate. The cells were grown at 37° C. The culture conditions of oxygen saturation 20% +/−10% and pH 7.1+/−0.35 were kept constant during virus propagation process.

b. Propagation of Influenza Virus

VERO cells were infected with two different influenza strains, New Caledonia A/H1N1 and Panama A/H3N2, and propagated in the respective medium. At the end of the virus propagation process the clarified supernatant containing the virus was purified by ultracentrifugation. The harvests of the VERO cells culture with either solely yeast hydrolysate or with yeast and soy hydrolysate were compared on the basis of the volumetric antigen productivity (total SRD, single radial immunodiffusion) and the antigen content of the supernatant at the end of the run (density gradient purified antigen). The yields for both media formulations were compared and are summarized in Table 1.

TABLE 1

Comparison of product yield from VERO Influenza production in different media composition

| | SRD (µg/ml) | Protein (µg/ml) | SRD/ Protein | Dose/Liter (per strain) |
|---|---|---|---|---|
| Strain | | New Caledonia A/H1N1 | | |
| 1 g/L yeast hydrolysate + 3 g/l soy hydrolysate | 130 | 341 | 0.38 | 146 |
| 1 g/L yeast hydrolysate | 51 | 147 | 0.35 | 57 |
| Strain | | Panama A/H3N2 | | |
| 1 g/L yeast hydrolysate + 3 g/l soy hydrolysate | 130 | 233 | 0.56 | 103 |
| 1 g/L yeast hydrolysate | 44 | 117 | 0.38 | 35 |

The combination of yeast hydrolysate and soy hydrolysate shows a marked improvement over yeast hydrolysate alone.

c. Production of Poxvirus

VERO cells were infected with a smallpox vaccine production strain (Dryvax, Wyeth Vaccines, obtained from Acambis, Inc., a calf-lymph vaccine strain adapted for growth in permanent cell line) adapted to growth in animal protein free VERO cells by serial passaging at a multiplicity of infection (m.o.i.) of 0.1-0.3. After an incubation time of 2-4 days at 37° C. the cells were harvested and virus was recovered from the cells.

Table 2 shows the results of virus yield obtained of cells grown in basal medium supplemented with yeast hydrolysate alone or with yeast and soy hydrolysate.

TABLE 2

Determination of Vaccinia virus titer at the end of the production cycle in th bioreactor system.

| Medium supplement | moi | Final Titer (pfu) | Pfu/Cell |
|---|---|---|---|
| 1 g/l yeast hydrolysate | 0.1-0.3 | $1.42 \times 10^7$/ml | 14 |
| 1 g/l yeast hydrolysate + 3 g/l soy hydrolysate | 0.1-0.3 | $16.00 \times 10^7$/ml | 69 |

The combination of yeast hydrolysate and soy hydrolysate shows a marked improvement over yeast hydrolysate alone.

d. Production of Ross River Virus

VERO cell culture obtained as described herein were infected with Ross River Virus at a multiplicity of infection (m.o.i.) of 0.1-0.3. After an incubation time of 2-4 days at 37° C., the cells were harvested and virus was recovered from the cells. Table 3 shows the results of virus yield obtained of cells grown in basal medium supplemented with yeast hydrolysate alone or with yeast and soy hydrolysate.

TABLE 3

Determination of Ross River Virus titer at the end of the production cycle in the bioreactor system.

| Medium supplement | Final Titer (pfu/ml) | Relative Yield (%) |
|---|---|---|
| 1 g/l yeast hydrolysate | $1.5. \times 10^7$ | 100 |
| 1 g/l yeast hydrolysate + 3 g/l soy hydrolysate | $2.5 \times 10^7$ | 167 |

The combination of yeast hydrolysate and soy hydrolysate shows a marked improvement over yeast hydrolysate alone.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

What is claimed is:

1. A method of cultivating mammalian surface-dependent cells to obtain a confluent cell culture, comprising:
   providing an animal protein-free medium comprising soy hydrolysate at a concentration of about 0.05% (w/v) to about 1% (w/v) and yeast hydrolysate at a concentration of about 0.05% (w/v) to about 0.3% (w/v);
   growing the surface-dependent cells in the medium; and
   passaging and sub-cultivating the cells grown in the medium in order to obtain a confluent cell culture;

wherein the cells are infected with an orthomyxovirus and are selected from the grouping consisting of BSC-1 cells, CV-1 cells, COS cells, VERO cells, MDBK cells, MDCK cells, MDOK cells, BHK-21 cells, WI-38 cells, and MRC-5 cells.

2. The method of claim 1, wherein the cells are recombinant cells.

3. The method of claim 1, wherein the virus is an influenza virus.

4. The method of claim 1, wherein the step of passaging and sub-cultivating the cells further comprises contacting the cells with a non-animal protease, wherein the protease is a purified trypsin-like fraction of *Strepomyces griseus* (SGT).

5. The method of claim 1, wherein the soy hydrolysate is present in a concentration of between about 0.2% (w/v) to about 0.6% (w/v) and the yeast hydrolysate is present in a concentration of between about 0.05% (w/v) to about 0.2% (w/v).

6. The method of claim 1, wherein the soy hydrolysate is present in a concentration of between about 0.25% (w/v) to about 0.35% (w/v) and the yeast hydrolysate is present in a concentration of between about 0.05% (w/v) to about 0.15% (w/v).

7. The method of claim 1, wherein the soy hydrolysate is present in a concentration of about 0.3% (w/v) and the yeast hydrolysate is present in a concentration of about 0.1% (w/v).

8. The method of claim 1, wherein 3 parts by weight soy hydrolysate are present to 1 part of weight yeast hydrolysate.

9. The method of claim 1, wherein the yeast hydrolysate is an ultrafiltered purified yeast hydrolysate, and wherein at least 40% of said yeast hydrolysate has a molecular weight of less than or equal to 500 Daltons.

10. The method of claim 1, wherein the soy hydrolysate is an ultrafiltered purified soy hydrolysate, and wherein at least 40% of said soy hydrolysate has a molecular weight of less than or equal to 500 Daltons.

11. The method of claim 1, wherein the cells grow on a carrier.

12. The method of claim 10, wherein the carrier is a synthetic carrier, or a microcarrier coated with a non-animal material.

* * * * *